(12) United States Patent
Kaul et al.

(10) Patent No.: US 7,087,677 B2
(45) Date of Patent: Aug. 8, 2006

(54) COPOLYMER COMPOSITION HAVING PIGMENT LIKE PROPERTIES

(75) Inventors: Bansi Lal Kaul, Biel-Benken (CH); Jean-Christophe Graciet, Huningue (FR); Mitchell A. Winnik, 486 Glenlake Avenue, Toronto, Ontario (CA) M6P 1G8; Frederic Tronc, Via 1° Maggio 80, 20020, Ceriano Laghetto (MI) (IT); Mei Li, 124 Edward Street, Room 460C, Toronto, ON (CA) M5G IG6; Jianping Lu, 1105-981 Gulf Place, Ottawa, ON (CA) K1K 3X9

(73) Assignees: Mitchell A. Winnik, Ontario (CA); Frederic Tronc, Paris (FR); Jianping Lu, Otario (CA); Mei Li, Ontario (CA)

( * ) Notice: Subject to any disclaimer, the term of this patent is extended or adjusted under 35 U.S.C. 154(b) by 0 days.

(21) Appl. No.: 10/467,708

(22) PCT Filed: Feb. 20, 2002

(86) PCT No.: PCT/IB02/00519

§ 371 (c)(1),
(2), (4) Date: Aug. 12, 2003

(87) PCT Pub. No.: WO02/066483

PCT Pub. Date: Aug. 29, 2002

(65) Prior Publication Data

US 2004/0063889 A1    Apr. 1, 2004

(30) Foreign Application Priority Data

Feb. 21, 2001 (GB) ................................ 0104240.7

(51) Int. Cl.
*C08L 31/00* (2006.01)

(52) U.S. Cl. ...................... 524/827; 524/832; 526/262; 526/265; 526/268; 526/288; 526/328.5

(58) Field of Classification Search ................ 526/262, 526/265, 268, 288, 328.5; 524/827, 832
See application file for complete search history.

(56) References Cited

U.S. PATENT DOCUMENTS 4,316,032 A  2/1982  Bitterli ........................ 548/109
4,526,963 A  7/1985  Deur ........................... 544/74
4,623,397 A  11/1986  Kaul ........................... 106/308
4,686,166 A  8/1987  Kumagai et al. ............ 430/109
5,021,573 A  6/1991  Bitterli et al. ............... 544/284
5,510,403 A  4/1996  Kaul ........................... 524/90
5,747,206 A  5/1998  Agata et al. .................. 430/64
6,103,006 A  8/2000  DiPietro ...................... 106/493
6,339,084 B1  1/2002  Kaul et al. ................ 514/224.2
6,375,732 B1  4/2002  Kaul et al. ................... 106/494

FOREIGN PATENT DOCUMENTS

| EP | 0 443 574 | 8/1991 |
| JP | 09-114120 | 2/1997 |
| WO | WO 99/21937 | 5/1999 |
| WO | WO 99/53920 | 10/1999 |
| WO | WO 00/31039 | 6/2000 |

OTHER PUBLICATIONS

"Copolymerization of Naphthalimidoalkylmethacrylates with Styrene and Fluorescence Behavior of Their Copolymers", Kim et al., Polymer (Korea), vol. 18, No. 3, pp. 285-291, (1994). English Abstract.

Synthesis and Fluorescence Behavior of Poly (ω-(1, 8-naphthalimido)alkyl methacrylates), Kim et al., Polymer Journal, vol. 26, No. 4, pp. 397-402 (1994).

"Vinyl Monomers Bearing Chromophore Moieties and their Polymers. XII. Synthesis and Fluorescence Behavior of Vinyloxy Monomers Having 1,8-naphthalimide Moiety with Different Spacer Lengths and Their Polymers", Polymers For Advanced Technologies, vol. 11, pp. 798-804 (2000).

English abstract for JP 09-114120.

*Primary Examiner*—Helen L. Pezzuto
(74) *Attorney, Agent, or Firm*—Ogilvy Renault LLP

(57) ABSTRACT

This invention relates to copolymer compositions having pigment like properties, comprising a fluorescent or non-fluorescent dye attached to a polymer chain by a spacer having a chain length of $C_3$ or longer.

The invention also provides for new mono- and difunctional dye monomers comprising a polymerizable group attached to a dye moiety by a spacer of a chain length of $C_3$ or longer.

The polymer pigments provide excellent properties, especially high temperature stability and easy applicability as colorant in different standard polymers.

15 Claims, No Drawings

COPOLYMER COMPOSITION HAVING PIGMENT LIKE PROPERTIES

This invention relates to copolymer compositions having pigment like properties, comprising a fluorescent or non-fluorescent dye attached to a polymer chain by a spacer. The invention also relates to the respective new dye monomers.

Articles containing colorants are known to loose their colour when exposed to solar radiation for extended times. In particular, fluorescent colorants degrade more quickly than conventional colorants, often turning colourless on exposure to daily solar radiation within days or months.

Colorants not covalently bond in a polymer matrix tend to agglomerate and to crystalize leading to inhomogeneous distribution of colorants within the matrix. Fluorescent colorants in particular often loose their fluorescent properties by agglomeration of fluorescent sites (quenching). Furthermore with non covalently bond colorants, fading or bleeding of the colorant occurs.

U.S. Pat. No. 6,103,006 (DiPietro) discloses fluorescent polymeric pigments with increased lightfastness obtained by the polycondensation of dye monomers with at least two functional groups like diamine, dialcohol or dicarboxylic acid. The functional groups for the polycondensation are directly located at the dye moiety as in the anhydride or diacid form of the BXDA fluorescent dye.

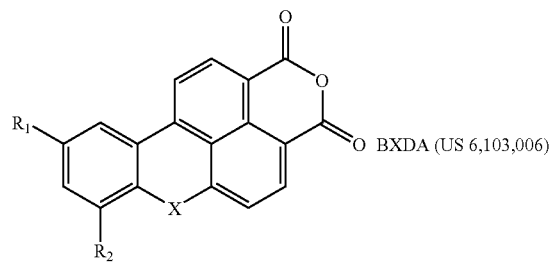

BXDA (US 6,103,006)

The physical properties of polymers depend highly on the structure of the polymerisable moiety and the process of polymerisation. Besides the above mentioned polycondensation process the polyreaction of chain growth polymers can be utilised to react dye monomers into a polymer backbone.

WO 99/21937 (3M) discloses a two phase interpenetrating polymer network system with a dye functionalized polymer in the second phase. The optionally fluorescent dye is covalently bond to the polymer to slow migration and to enhance compatibility, e.g. a hydroxy functional dye (YGOH) is reacted into a polyurethane or an acrylate functional dye (YGOAcr) is reacted into a respective chain growth polymer.

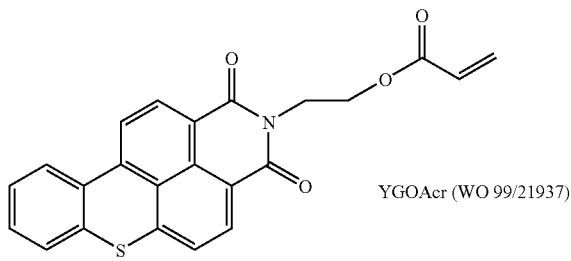

YGOAcr (WO 99/21937)

The preferred fluorescent dye moieties are thioxanthene and perylene imide, at a content of 0.01 to 2 percent by weight (based on the total composition).

Other structures known to have dye properties are disclosed in WO 00/31039 in a completely different context: as pharmaceutically active compounds for the control of thrombotic disorders and for use as anti-adhesive substances for implants, catheters or heart pacemakers. The substituents are selected in view of pharmaceutical activity and applicability and the substituted benzo[de]isoquinoline-1,3-diones are not supposed to have any connective functionality in the sense of a copolymerizable monomer.

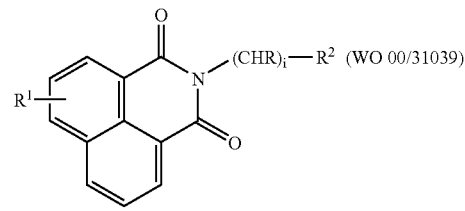

(WO 00/31039)

A problem of copolymerisation in general is, that each monomer has its own copolymerization parameters, in the extreme not being copolymerizable at all.

One objective of the invention is to allow variation of the dye moieties without significantly changing the copolymerization parameters of the dye monomers by separating the polymerizable moiety and the dye moiety from each other with a spacer. Further, the spacer is adjusted in chain length to enhance the dye properties in the matrix, especially the temperature stability and fluorescent properties, without significantly changing the physical polymer properties.

Another objective of the present invention is to provide a copolymer composition polymerising to fine, uniform, regular copolymer particles in suspension polymerisation.

A further objective of the present invention is to provide a new copolymer with pigment like properties being easily applicable in the coloration of standard polymers.

These objectives are achieved by a copolymer composition comprising a new dye monomer, in which the dye moiety of the monomer is separated from the polymerizable moiety by a spacer having a chain length of $C_3$ or longer, preferably of $C_6$.

The dye monomer is of the general formula (I)

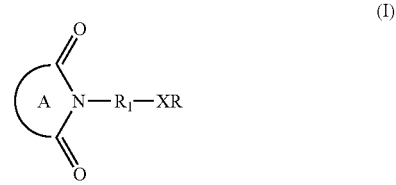

wherein $R_1$ is $C_{3-6}$ alkylene, $C_{3-6}$ alkoxylene, $C_{6-10}$ arylene, $(C_{6-10})$ aryl-$(C_{1-6})$ alkylene or $(C_{1-6})$ alkyl-$(C_{6-10})$ arylene, the alkylene and/or arylene radicals optionally being substituted by hydroxyl, $C_{1-6}$ alkoxyl, $C_{6-10}$ aryloxy or halogen, X is oxygen or NR' with R' being $C_{1-6}$ alkyl, $C_{6-10}$ aryl, $(C_{6-10})$ aryl-$(C_{1-6})$ alkyl or $(C_{1-6})$ alkyl-$(C_{6-10})$ aryl, the alkyl and/or aryl radicals optionally being substituted by hydroxyl, $C_{1-6}$ alkoxyl, $C_{6-10}$ aryloxy or halogen, R is a polymerizable group selected from methylmethacrylate or methacrylate, and A is a fused heterocyclic ring system of the general formula (IV)

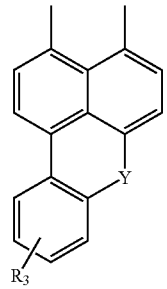

wherein $R_3$ is hydrogen, halogen, $NR_4R_5$, $R_5O$ or $R_5S$, with $R_4$ being hydrogen, $C_{1-6}$ alkyl, $C_{6-10}$ aryl, $(C_{6-10})$ aryl-$(C_{1-6})$ alkyl or $(C_{1-6})$ alkyl-$(C_{6-10})$ aryl, the alkyl and/or aryl radicals optionally being substituted by hydroxyl, $C_{1-6}$ alkoxyl, $C_{6-10}$ aryloxy or halogen; $R_5$ being $C_{1-6}$ alkyl, $C_{6-10}$ aryl, $(C_{6-10})$ aryl-$(C_{1-6})$ alkyl or $(C_{1-6})$ alkyl-$(C_{6-10})$ aryl, the alkyl and/or aryl radicals optionally being substituted by hydroxyl, $C_{1-6}$ alkoxyl, $C_{6-10}$ aryloxy or halogen; and Y being sulphur, oxygen or $NR_4$, with $R_4$ having the meaning given above.

Especially preferred dye monomers are those of the general formula (I) where A is of the general formula (IV). Further especially preferred dye momomers are of the general formula (I) with A being of formula (IV) and Y being sulphur and $R_3$ being hydrogen.

The preferred spacer $R_1$ is a $C_{4-6}$ alkylene or $C_{3-6}$ alkoxylene, most preferably $C_6$ alkylene or ethoxy-ethoxy-ethylene.

The preferred polymerizable groups for R is methylmethacrylate.

Preferred co-monomers for the copolymer composition are methacrylate, methylmethacrylate, styrene and vinyl type monomers.

The preferred content of the dye monomer in a copolymer composition according to the invention is from 0.01 to 10, more preferably from 1 to 5 and most preferably between 2 and 3 percent by weight based on the total weight of the copolymer composition.

The dye monomers of formulae (I) are obtained by the condensation of the dicarboxylic anhydride of the respective dye moiety with an amino alcohol or a diamine comprising the respective spacer in a polar aprotic solvent.

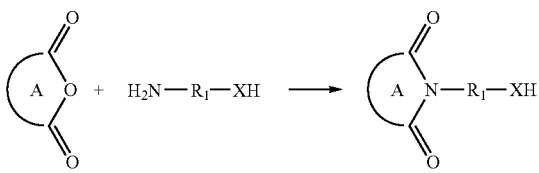

The hydroxy or amino group on the free end of the spacer can be further functionalized under acid or basic conditions with acrylic or methacrylic acid or derivatives thereof, such as the acid chloride. The final product is obtained in high yield.

The general synthesis is shown in the scheme below

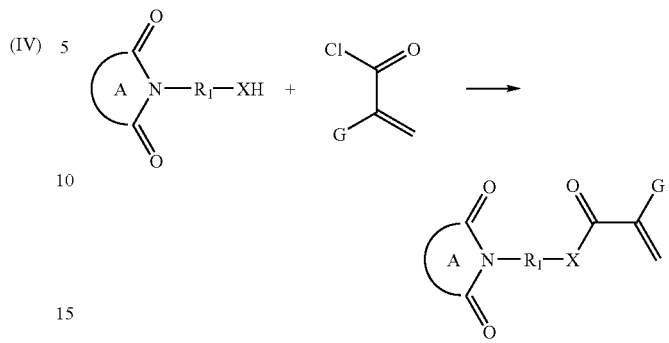

wherein A, $R_1$ and X are as defined above and G is hydrogen or methyl.

The copolymerization of the dye monomers according to the invention is usually carried out as a radical initiated suspension (or miniemulsion) polymerisation in water, together with the respective chain growth monomer, such as acrylate, methacrylate, styrene or vinyl type co-monomers. The copolymer is obtained as fine latex particles of very uniform and regular shape.

The range of particle size obtained by this copolymerization process is 10 to 500 nm, preferably 20 to 200 nm and most preferably from 40 to 150 nm.

The copolymer pigments according to the invention are suitable for the mass pigmentation of substrates including synthetic polymers, synthetic resins and regenerated fibres optionally in the presence of solvents. These substrates more particularly include oil, water and solvent based surface coatings, polyester spinning melts, polyethylene, polystyrene and polyvinyl chloride melts, polymethacrylate and polymethylmethacrylate melts, polyurethane masses, rubber and synthetic leather. Furthermore, the pigments can be used in the manufacture of printing inks, for the mass coloration of paper and for coating and printing textiles.

The copolymer pigments according to the invention are also suitable as colorants in electrophotographic toners and developers, such as one- or two-component powder toners (also called one- or two-component developers), magnetic toners, liquid toners, polymerisation toners and speciality toners.

Typical toner binders are addition polymerisation, polyaddition and polycondensation resins, such as styrene, styrene-acrylate, styrene-butadiene, acrylate, polyester and phenol-epoxy resins, polysulphones, polyurethanes, individually or in combination, and also polyethylene and polypropylene, which may comprise further constituents, such as charge control agents, waxes or flow assistants, or may be modified subsequently with these additives.

The copolymer pigments according to the invention are suitable, furthermore, as colorants in powders and powder coating materials, especially in triboelectrically or electrokinetically sprayable powder coating materials which are used for the surface coating of articles made, for example, from metal, wood, plastic, glass, ceramic, concrete, textile material, paper or rubber.

Powder coating resins that are typically employed are epoxy resins, carboxyl- and hydroxyl-containing polyester resins, polyurethane resins and acrylic resins, together with customary hardeners. Combinations of resins are also used. For example, epoxy resins are frequently employed in combination with carboxyl- and hydroxyl-containing polyester resins. Typical hardener components (as a function of the resin system) are, for example, acid anhydrides, imidazoles and also dicyanodiamide and its derivatives, blocked isocyanates, bisacylurethanes, phenolic and melamine resins, triglycidyl isocyanurates, oxazolines and dicarboxylic acids.

In addition, the copolymer pigments according to the invention are suitable as colorants in ink-jet inks, both aqueous and non-aqueous, and in those inks, which operate in accordance with the hot-melt process.

The following examples illustrate the invention. Unless otherwise specified, parts and percentages used in the examples are on a weight to weight basis.

COMPARATIVE EXAMPLE 1

Synthesis of HY2MA Monomer

Benzothioxanthene dicarboxylic anhydride (10 parts) is condensed to ethanolamine (3 parts) at room temperature under nitrogen atmosphere. After reaction completion at same temperature, the resulting mixture is poured into 40 parts of water and stirred for further 30 minutes. Orange suspension is then filtered, washed with water until no amine is detectable in filtrate. After drying, 11 parts are obtained as a bright orange powder (98% yield).

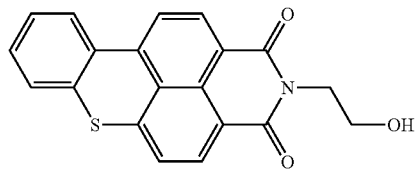

20 parts of this hydroxy functionalized compound are suspended into 75 parts of o-dichlorobenzene in presence of 6.1 parts of triethylamine. The mixture is then heated to 130° C. and methacryloyl chloride (6.3 parts) is added over 45 minutes at this temperature. After reaction completion, the resulting red solution is cooled to room temperature and filtered. The presscake is then washed with methanol and dried. 21 parts of bright orange powder are obtained (yield 93%).

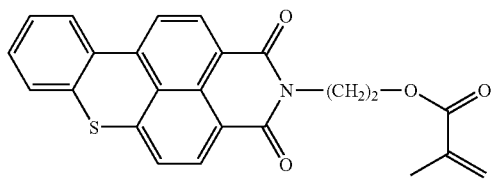

EXAMPLE 2

Synthesis of HY6MA Monomer

Benzothioxanthene dicarboxylic anhydride (10 parts) is condensed to 6-aminohexanol (6 parts) in dimethylformamide (6 parts) in presence of catalytic para-toluenesulfonic acid (0.1 part) at 130° C. under nitrogen atmosphere.

When the reaction is complete, the resulting mixture is cooled to 60° C. and 3 parts of methanol are added. After cooling to room temperature, the final product is filtered, washed with methanol and dried. 12 parts of bright orange powder are obtained (93% yield).

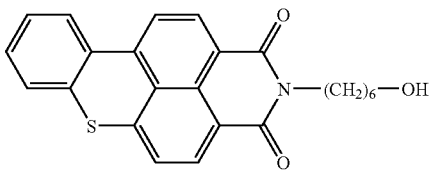

20 parts of this hydroxy functionalized compound are suspended into 75 parts of o-dichlorobenzene in presence of 5.0 parts of triethylamine. The mixture is then heated to 130° C. and methacryloyl chloride (5.2 parts) is added over 45 minutes at this temperature. After reaction completion, the resulting red solution is cooled to room temperature and filtered. The presscake is washed with methanol and dried. 20 parts of bright orange powder are obtained (yield 90%).

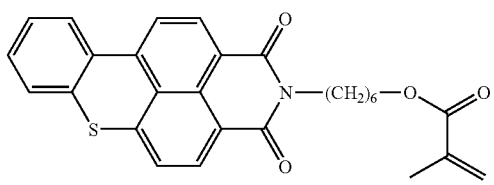

EXAMPLE 3

Synthesis of HY-E3N-MA 3 Monomer 2,2'-(ethylenedioxy)-diethylamine (40 parts) are heated to 70° C. under nitrogen atmosphere. Benzothioxanthene anhydride (10 parts) is slowly added at this temperature over a period of 3 hours. After reaction completion, 40 parts of water are added and the resulting mixture is stirred at 70° C. for 30 minutes. The suspension is then filtered, washed with water and dried. 10 parts of orange powder are obtained (yield 80%).

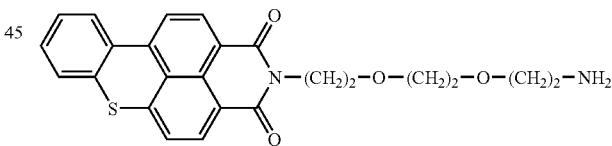

20 parts of this amine functionalized compound are suspended into 50 parts of o-dichlorobenzene in presence of 5.0 parts of triethylamine. The mixture is then heated to 130° C. and methacryloyl chloride (5.2 parts) is added over 45 minutes at this temperature. After reaction completion, the resulting red solution is cooled to room temperature and filtered. The presscake is washed with methanol and dried. 18 parts of bright orange powder are obtained.

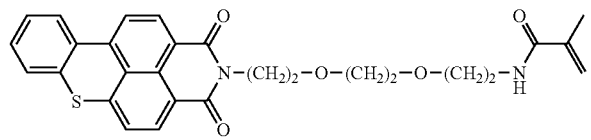

COMPARATIVE EXAMPLE 4

Synthesis of PS-co-HY2MA Copolymer

1. Copolymerization

To a 3 neck 250 ml round bottom flask equipped with a condenser and a gas inlet, HY2MA (6.0 g, 14.5 mmol), styrene (4.0 g, 38.5 mmol), AIBN (1 wt % based on monomers) and chloroform (100 ml) were added. The mixture was stirred and degassed by nitrogen for 30 minutes. Copolymerization of HY2MA and styrene was carried out at 60° C. for 12 hours. The copolymer precipitated spontaneously during the polymerisation reaction. The reaction was terminated by the addition of tiny amount of inhibitor 2,6-di-tert-butyl-4-methylphenol.

2. Purification

The precipitate was collected and mixed with chloroform. The mixture was stirred for 15 minutes. The supernatant solutions was discarded. This step was repeated for 3 times to remove unreacted HY2MA monomer and soluble copolymer. The Copolymer was then immersed in dimethylformamide (DMF) overnight to well the polymer to aid in removal of soluble components trapped in the mixture. Insoluble copolymer was collected by filtration after it was washed with DMF for 5 minutes followed by filtration. The precipitate was dried in a vacuum oven at 40° C. overnight.

3. Properties

Shape and colour: 5.5 g orange powder

Solubility: insoluble in the following organic solvents: methanol, acetone, THF, DMF, DMSO, chloroform Composition: according to the monomer feed composition and the reactivity ratios of the monomers, the copolymer composition was calculated from the copolymer composition equation. It should contain 43.2 mol % of HY2MA and 66.8 mol % of styrene. However, the copolymer is actually a mixture of PS-co-HY2MA copolymers with different copolymer compositions. With the increase of the conversion during the polymerisation, the more reactive monomer HY2MA was consumed. This results in a continual shift of the monomer feed composition to lower HY2MA content, and also a continual shift in copolymer composition. The calculated copolymer composition can only be obtained at low conversions of polymerisation (<10%) where the compositional drift is negligible.

EXAMPLE 5

Synthesis of PS-co-HY6MA Cross-Linked Latex Particles

1. Copolymerization

To a 3 neck 250 ml round bottom flask equipped with a condenser and a gas inlet, deionized water (40 g), Triton X405 (20 g, 70% aqueous solution), cross-link reagent divinylbenzene (1.58 g, 80% purity) and dye monomer HY6MA (0.9 g) dissolved in styrene (29.1 g) were added under stirring. The mixture was stirred and degassed by nitrogen for 30 minutes. After the mixture was heated to 70° C., potassium persulfate aqueous solution (10 ml, 0.3 g/mL) was added into the system to initiate the polymerisation. The reaction was terminated 24 hours later by cooling down the reaction mixture to room temperature.

2. Characterisation of the Latex Particles

Particle sizes and polydispersity were measured by the BI-90 Particle sizer. The molecular mass of the latex particles was estimated from its size and polymer density. The dye content of the latex particles was determined by UV-VIS measurement of the purified latex particles in chloroform using the extinction coefficient of HY6MA in chloroform ($\epsilon_{460nm}$=4.82×10$^4$ ml/g.cm). Water was removed from latex dispersion by freeze drying. The latex particles were washed with methanol 8 times to remove surfactant. The results are listed in the following table:

| Diam./nm | Poly-dispersity | Molar mass (g/mol) | Dye-content | Cross-link density (mol %) |
|---|---|---|---|---|
| 52 | 0.065 | 4.61 × 10$^7$ | 2.7 wt % or 5.73 × 10$^{-5}$ mol/g polym. | 6.5 |

EXAMPLE 6

Synthesis of PMMA-co-HY6MA Cross-Linked Latex Particles

1. Copolymerization

First an aqueous solution was created by mixing sodium dodecyl sulphate (1.6 g), NaHCO$_3$ (0.09 g) and deionized water (160 g). Then the dye monomer (HY6MA, 1.21 g) was mixed with the oil phase containing MMA (36.8 g), divinyl benzene (2.0 g) and hexadecane (1.45 g). When the dye monomer was completely dissolved, the oil and aqueous phases were mixed in a beaker for 20 min. The resulting emulsion was then sonified for 60 s. The resulting miniemulsion was added to a 3 neck 250 ml round bottom flask equipped with a condenser and a gas inlet. After bubbling the miniemulsion with nitrogen for 30 min and heating it to 75° C., potassium persulphate (0.4 g) in deionized water was added. The reaction was kept overnight.

2. Characterisation of the Latex Particles

Particle sizes and polydispersity were measured by the BI-90 Particle sizer. The molecular mass of the latex particles was estimated from its size and polymer density. The dye content of the latex particles was determined by UV-VIS measurement of the purified latex particles in chloroform using the extinction coefficient of HY6MA in chloroform ($\epsilon_{460nm}$=4.82×10$^4$ ml/g.cm). Water was removed from latex dispersion by freeze drying. The latex particles were washed with methanol 3 times to remove surfactant and unattached dye. The results are listed in the following table:

| Diam./nm | Poly-dispersity | Molar mass (g/mol) | Dye-content | Cross-link density (mol %) |
|---|---|---|---|---|
| 105 | 0.16 | 3.79 × 10$^8$ | 2.83 wt % | 6.2 |

EXAMPLE 7

Synthesis of PS-MAA-co-HY6MA Cross-Linked Latex Particles

1. Copolymerization

First an aqueous solution was created by mixing sodium dodecyl sulphate (1.6 g), NaHCO$_3$ (0.8 g) and deionized water (160 g). Then the dye monomer (HY6MA, 1.20 g) was mixed with the oil phase containing styrene (36.1 g), methylacrylic acid (0.82 g), divinyl benzene (2.0 g) and hexadecane (1.45 g). When the dye monomer was completely dissolved, the oil and aqueous phases were mixed in a beaker for 20 min. The resulting emulsion was then sonified for 60 s. The resulting miniemulsion was added to a 3 neck 250 ml round bottom flask equipped with a condenser and a gas inlet. After bubbling the miniemulsion with nitrogen for 30 min and heating it to 75° C., a potassium persulphate (0.4 g) in deionized water was added. The reaction was kept overnight.

2. Characterisation of the Latex Particles

Particle sizes and polydispersity were measured by the BI-90 Particle sizer. The molecular mass of the latex particles was estimated from its size and polymer density. The dye content of the latex particles was determined by UV-VIS measurement of blend films. To obtain the films, the particles were dispersed in THF and mixed with pure PS to make a PS/PS-MAA-HY6MA blend solution. The blend was precipitated from methanol and dried in a vacuum oven overnight before a series of blend films with different thickness were made. The results are listed in the following table:

| Diam./nm | Poly-dispersity | Molar mass (g/mol) | Dye-content | Cross-link density (mol %) |
|---|---|---|---|---|
| 102 | 0.07 | $3.48 \times 10^8$ | 2.76 wt % | 6.4 |

The invention claimed is:

1. Copolymer particles of a copolymer dye composition, comprising at least one dye monomer, wherein the dye monomer is of the general formula (I)

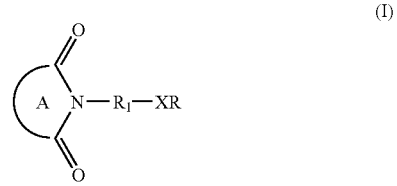

(I)

wherein R$_1$ is C$_{3-6}$ alkylene, C$_{3-6}$ alkoxylene, C$_{3-10}$ arylene, (C$_{3-10}$) aryl-(C$_{1-6}$) alkylene or (C$_{1-6}$) alkyl-(C$_{6-10}$) arylene, the alkylene and/or arylene radicals optionally being substituted by hydroxyl, C$_{1-6}$ alkoxyl, C$_{6-10}$ aryloxy or halogen, X is oxygen or NR' with R' being C$_{1-6}$ alkyl, C$_{6-10}$ aryl, (C$_{6-10}$) aryl-(C$_{1-6}$) alkyl or (C$_{1-6}$) alkyl-(C$_{6-10}$) aryl, the alkyl and/or aryl radicals optionally being substituted by hydroxyl, C$_{1-6}$ alkoxyl, C$_{6-10}$ aryloxy or halogen, R is selected from the group comprising an acrylate moiety or a methacrylate moiety and derivatives thereof, A is a fused heterocyclic ring system of the general formula (IV)

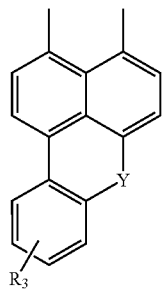

(IV)

wherein R$_3$ is hydrogen, halogen, NR$_4$R$_5$, R$_5$O or R$_5$S, in which

R$_4$ is hydrogen, C$_{1-6}$ alkyl, C$_{6-10}$ aryl, (C$_{6-10}$) aryl-(C$_{1-6}$) alkyl or (C$_{1-6}$) alkyl-(C$_{6-10}$) aryl, the alkyl and/or aryl radicals optionally are substituted by hydroxyl, C$_{1-6}$ alkoxyl, C$_{6-10}$ aryloxy or halogen;

R$_5$ is C$_{1-6}$ alkyl, C$_{6-10}$ aryl, (C$_{6-10}$) aryl-(C$_{1-6}$) alkyl or (C$_{1-6}$) alkyl-(C$_{6-10}$) aryl, the alkyl and/or aryl radicals optionally are substituted by hydroxyl, C$_{1-6}$ alkoxyl, C$_{6-10}$ aryloxy or halogen; and Y is sulphur, oxygen or NR$_4$, in which R$_4$ has the meaning given above, copolymerized with at least one copolymerizable monomer.

2. Copolymer particles according to claim 1 wherein R$_1$ has a chain length of C$_6$.

3. Copolymer particles according to claim 1, wherein the at least one copolymerizable monomer is a monomer of the methacrylate, methylmethacrylate, styrene or vinyl type.

4. Copolymer particles according to claim 1, wherein the content of the dye monomer in the copolymer particles is between about 0.01 and 10 percent by weight.

5. A pigment comprising the copolymer particles according to claim 1.

6. A polymer product comprising a pigment according to claim 5.

7. Copolymer particles according to claim 1, wherein the content of the dye monomer is between 2 and 3 percent by weight.

8. Copolymer particles of a copolymer dye composition according to claim 1, wherein the copolymer particles have a mean diameter in the range of about 10 to about 500 nm and are of uniform distribution.

9. Copolymer particles of a copolymer dye composition according to claim 1, wherein the dye monomer is of the formula (HY6MA)

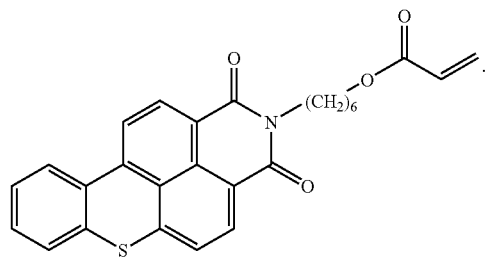

HY6MA

10. A process for the preparation of copolymer particles of a copolymer dye composition comprising subjecting at least one dye monomer of the general formula (I)

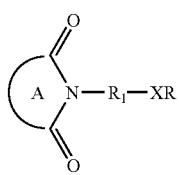

(I)

wherein $R_1$ is $C_{3-6}$ alkylene, $C_{3-6}$ alkoxylene, $C_{3-10}$ arylene, $(C_{3-10})$ aryl-$(C_{1-6})$ alkylene or $(C_{1-6})$ alkyl-$(C_{6-10})$ arylene, the alkylene and/or arylene radicals optionally being substituted by hydroxyl, $C_{1-6}$ alkoxyl, $C_{6-10}$ aryloxy or halogen, X is oxygen or NR' with R' being $C_{1-6}$ alkyl, $C_{6-10}$ aryl, $(C_{6-10})$ aryl-$(C_{1-6})$ alkyl or $(C_{1-6})$ alkyl-$(C_{6-10})$ aryl, the alkyl and/or aryl radicals optionally being substituted by hydroxyl, $C_{1-6}$ alkoxyl, $C_{6-10}$ aryloxy or halogen, R is selected from the group comprising an acrylate moiety or a methacrylate moiety and derivatives thereof, A is a fused heterocyclic ring system of the general formula (IV)

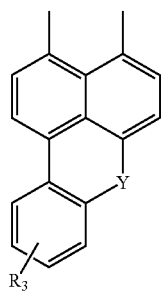

(IV)

wherein $R_3$ is hydrogen, halogen, $NR_4R_5$, $R_5O$ or $R_5S$, in which $R_4$ is hydrogen, $C_{1-6}$ alkyl, $C_{6-10}$ aryl, $(C_{6-10})$ aryl-$(C_{1-6})$ alkyl or $(C_{1-6})$ alkyl-$(C_{6-10})$ aryl, the alkyl and/or aryl radicals optionally are substituted by hydroxyl, $C_{1-6}$ alkoxyl, $C_{6-10}$ aryloxy or halogen;

$R_5$ is $C_{1-6}$ alkyl, $C_{6-10}$ aryl, $(C_{6-10})$ aryl-$(C_{1-6})$ alkyl or $(C_{1-6})$ alkyl-$(C_{6-10})$ aryl, the alkyl and/or aryl radicals optionally are substituted by hydroxyl, $C_{1-6}$ alkoxyl, $C_{6-10}$ aryloxy or halogen; and Y is sulphur, oxygen or $NR_4$, in which $R_4$ has the meaning given above, and at least one copolymerizable monomer to suspension polymerization.

11. A process according to claim 10 comprising the step of mixing the at least one dye monomer with the at least one copolymerizable monomer before the suspension polymerization.

12. A process according to claim 10 wherein $R_1$ a chain length of $C_6$.

13. A process according to claim 10 wherein the at least one copolymerizable monomer is a monomer of the methacrylate, methylmethacrylate, styrene or vinyl type.

14. A process according to claim 10 wherein the dye monomer is of the formula HY6MA

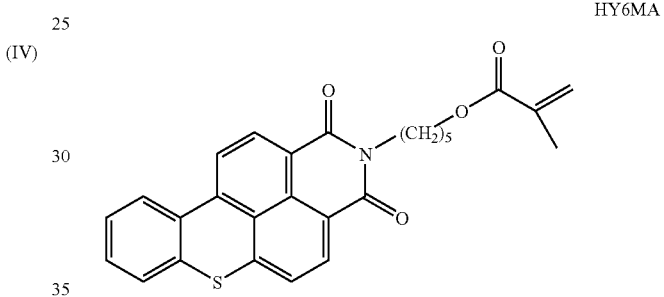

HY6MA

15. A process according to claim 10 wherein the suspension polymerization is a miniemulsion polymerization.

* * * * *